United States Patent
Fariss et al.

(10) Patent No.: US 6,682,503 B1
(45) Date of Patent: Jan. 27, 2004

(54) ANTI-REFLUX VALVE INTERCONNECTED WITH A CATHETER

(75) Inventors: Bruce L. Fariss, Knoxville, TN (US); Ivan N. Cooper, Knoxville, TN (US)

(73) Assignee: Ibionics, Inc., Knoxville, TN (US)

( * ) Notice: Subject to any disclaimer, the term of this patent is extended or adjusted under 35 U.S.C. 154(b) by 0 days.

(21) Appl. No.: 10/008,902

(22) Filed: Dec. 7, 2001

(51) Int. Cl.[7] .............. A61M 1/00; A61M 5/00; A61F 5/44; F16K 15/14
(52) U.S. Cl. .............. 604/34; 604/323; 604/326; 604/350; 604/247; 137/843
(58) Field of Search .............. 604/323, 326, 604/350, 34, 30, 508, 246, 247; 251/358; 137/511, 512, 855, 843, 846

(56) References Cited

U.S. PATENT DOCUMENTS

| | | | |
|---|---|---|---|
| 3,295,556 A | | 1/1967 | Gertsma et al. |
| 3,312,221 A | * | 4/1967 | Overment .............. 604/317 |
| 3,671,979 A | * | 6/1972 | Moulopoulos .............. 623/2.11 |
| 3,832,999 A | * | 9/1974 | Crilly .............. 604/185 |
| 3,967,645 A | * | 7/1976 | Gregory .............. 137/846 |
| 4,227,533 A | * | 10/1980 | Godfrey .............. 604/247 |
| 4,342,315 A | * | 8/1982 | Jackson .............. 604/35 |
| 4,512,770 A | | 4/1985 | Cianci et al. |
| 4,579,555 A | | 4/1986 | Russo |
| 4,629,159 A | * | 12/1986 | Wellenstam .............. 251/149.6 |
| 4,784,651 A | | 11/1988 | Hickey |
| 4,828,554 A | * | 5/1989 | Griffin .............. 604/350 |
| 4,968,294 A | * | 11/1990 | Salama .............. 600/30 |
| 5,045,075 A | | 9/1991 | Ersek |
| 5,098,418 A | * | 3/1992 | Maitz et al. .............. 604/319 |
| 5,148,811 A | * | 9/1992 | Messinger .............. 600/486 |
| 5,180,364 A | * | 1/1993 | Ginsburg .............. 604/510 |
| 5,356,386 A | * | 10/1994 | Goldberg et al. .............. 604/118 |
| 5,496,300 A | | 3/1996 | Hirsch et al. |
| 5,549,579 A | | 8/1996 | Batdorf et al. |
| 5,616,138 A | | 4/1997 | Propp |
| 5,660,205 A | * | 8/1997 | Epstein .............. 137/512.15 |
| 5,725,515 A | | 3/1998 | Propp |
| 5,728,078 A | * | 3/1998 | Powers, Jr. .............. 604/246 |
| 5,741,237 A | * | 4/1998 | Walker .............. 604/317 |
| 5,749,920 A | * | 5/1998 | Quiachon et al. .............. 623/1.23 |
| 5,807,349 A | * | 9/1998 | Person et al. .............. 604/247 |
| 5,919,146 A | | 7/1999 | Propp |
| 5,935,115 A | | 8/1999 | Espina |
| 5,989,288 A | * | 11/1999 | Pintauro et al. .............. 600/30 |
| 6,044,859 A | * | 4/2000 | Davis .............. 137/15.19 |
| 6,065,597 A | * | 5/2000 | Pettersson et al. .............. 206/364 |
| 6,156,019 A | * | 12/2000 | Langevin .............. 604/323 |
| 6,383,171 B1 | * | 5/2002 | Gifford et al. .............. 604/508 |

FOREIGN PATENT DOCUMENTS

DE  0 351 864 A1 * 7/1989 .......... A61M/25/00

* cited by examiner

Primary Examiner—Weilun Lo
Assistant Examiner—Michael Bogart
(74) Attorney, Agent, or Firm—Pitts & Brittain, P.C.

(57) ABSTRACT

An anti-reflux valve for restricting flow in one direction through a catheter toward a collection reservoir. The valve includes a check valve positioned within a segment of the catheter. The valve includes a proximal end bonded to an inside periphery of an interior of the catheter. The valve includes a pliable side wall that reduces in diameter to a distal end having an opening that is collapsible upon itself. Fluid flow is allowed through the catheter segment having the check valve therein, with flow only permitted from the proximal end and through the distal end for release into a collection reservoir. The distal end opening collapses upon itself to negate the counter-current flow of fluid through the distal end. A plurality of check valves are aligned in series to reduce the possibility of reflux flow of fluids. A method of utilization of the anti-reflux valve is also disclosed.

16 Claims, 3 Drawing Sheets

US 6,682,503 B1

ANTI-REFLUX VALVE INTERCONNECTED WITH A CATHETER

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention pertains to surgical drains for removal of fluid from a patient. More particularly, this invention pertains to a valve for one-way draining of fluids through a catheter attached to a patient.

2. Description of the Related Art

Prior catheter collection devices have provided conduits for fluid drainage from a body cavity of a patient including tubing and an externally connected valve for unidirectional flow of fluid into a collection receptacle. Typically the catheter is connected by a length of tubing to the externally connected valve that is manipulated by an attendant or the patient to purge the tubing of fluids by channeling flow into a collection receptacle such as a detachable bag. It is imperative to minimize the possibility of reflux to reduce the potential for infection in patients utilizing a urethral drainage catheter or a similar drainage conduit from a patient. A typical valve for a catheter allows for flow past the valve due to an upgradient liquid pressure in the catheter forcing liquid through the valve. Alternatively a shut-off clamp is manipulated by an attendant or the patient to allow drainage of the fluids through a catheter. Upon manipulation of the shut-off clamp, or during operation of the needle valve, there is an opportunity for reflux and passage of infectious materials upstream to the patient.

There is a need for an anti-reflux valve that forms a one-way drain valve within a catheter for drainage of fluids. A need exists for a discharge valve that may be incorporated with a like configured second discharge valve within a catheter. A further need is for an anti-reflux valve that is a self-contained conduit having at least one inline valve positioned within the conduit for ease of sterilization and for ease of use as a sterile unit that is packaged for rapid access and connection with a drainage catheter during a medical procedure in a sterile environment.

BRIEF SUMMARY OF THE INVENTION

According to one embodiment of the present invention, an anti-reflux valve is provided for control of flow through a catheter and toward a fluid collection reservoir. The anti-reflux valve includes a check valve positioned within a segment of a catheter, the check valve includes a proximal end that is substantially cylindrical and forms a junction bonded to the interior circumference of the catheter. The check valve includes a side wall that is continuous, composed of pliable material, and is reduced in diameter at a distal end having a circumferential opening that is collapsible upon itself upon the presence of counter-current fluid pressure. One-way flow of liquids from a patient is maintained through the segment of the catheter having the anti-reflux valve therein, with flow permitted through the proximal end of the check valve and through the distal end of the valve toward a tube connection with a fluid collection reservoir. Reverse flow through the distal end of the check valve is not allowed due to the closure of the opening of the distal end upon the presence of counter-current fluid against the pliable material of the distal end. The anti-reflux valve includes at least one check valve, or alternatively two or more check valves aligned in series within the catheter, with the distal end of a first check valve aligned with a proximal end of a second check valve, in a repetitive series of check valves leading toward the tube connection with the fluid collection reservoir. A method of utilization of the anti-reflux valve is also disclosed for use of at least one check valve within a drainage catheter as part of a medical procedure practiced in a sterile environment.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
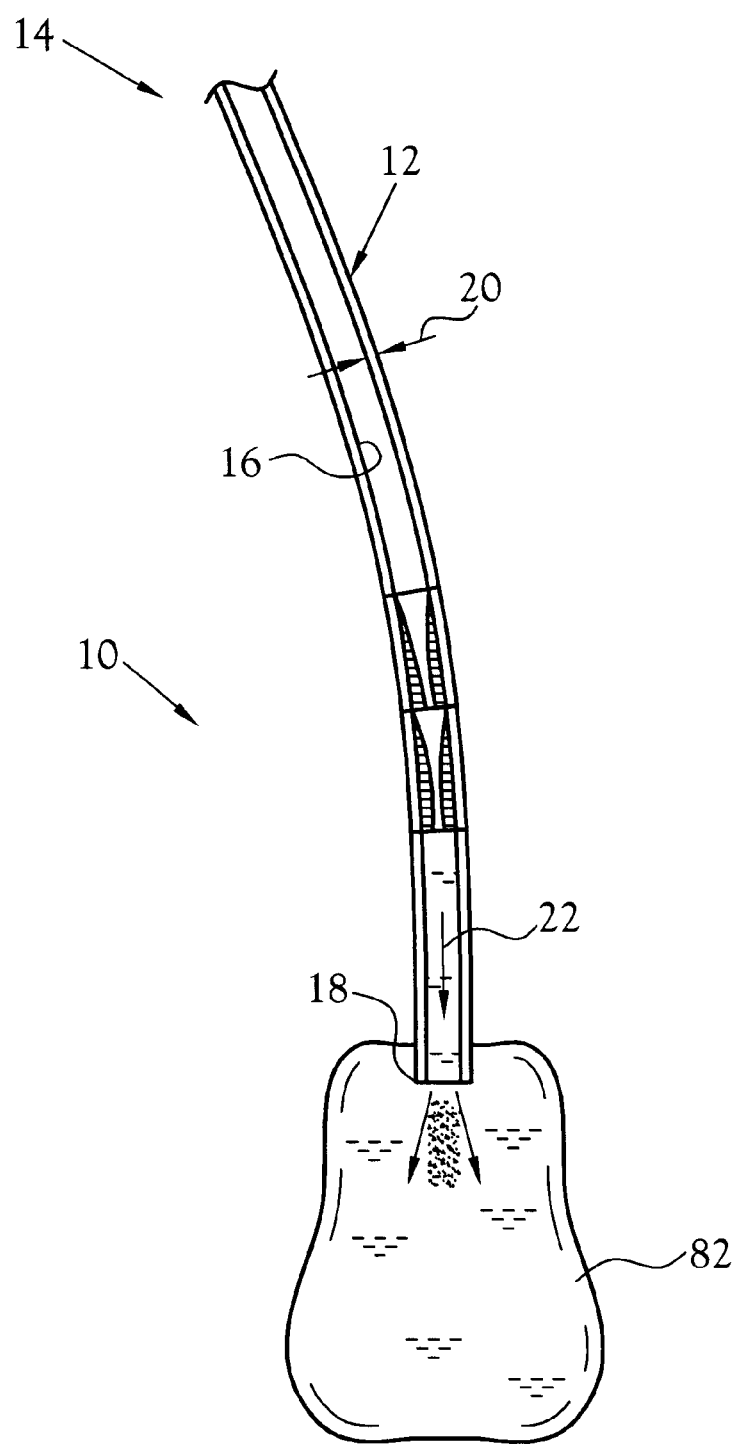
FIG. 1 is a side view of an anti-reflux valve of the present invention, positioned within a catheter connected to a collection reservoir.

An anti-reflux valve 10 is disclosed for connection within a tube such as a catheter for one-way passage of fluids from a patient for delivery to a fluid collection reservoir as illustrated in FIG. 1. The anti-reflux valve 10 provides protection from infection and contamination of a patient's internal body fluids due to potential exposure to external fluids refluxed from a collection reservoir. The anti-reflux valve 10 includes a catheter 12 having a first end 14 adapted to be inserted into a patient, and having a second end 18 adapted to be releasably attached to a collection reservoir 82. The walls 20 of the catheter are of a thickness applicable to the use associated with insertion into the patient.

Figure 2A:
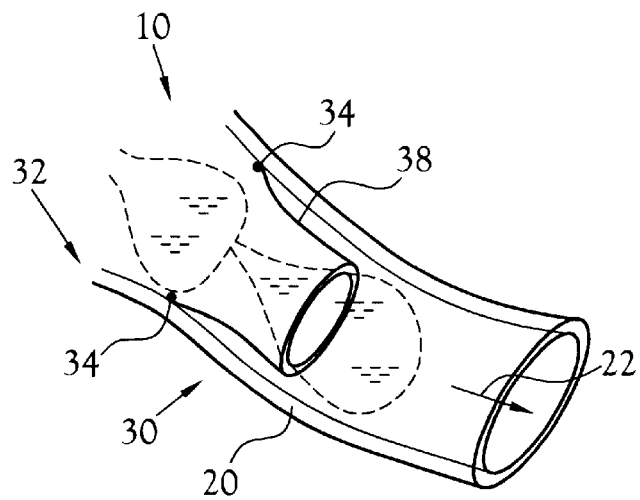
FIG. 2a is a perspective view of the anti-reflux valve, illustrating a distal end of a check valve in an open position to allow passage of fluid.
Figure 2B:
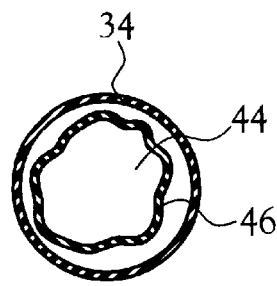
FIG. 2b is an end view of FIG. 2a, illustrating the distal end of the check valve in an open position.
Figure 3A:
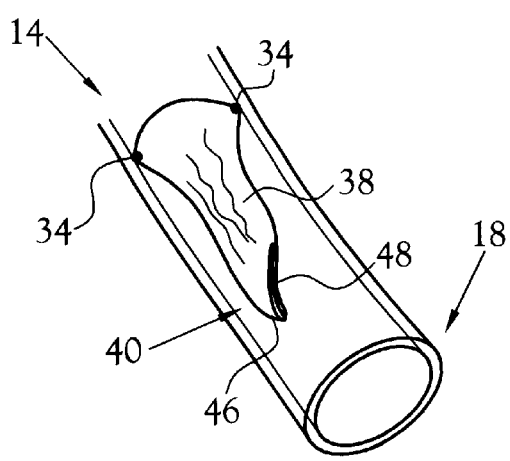
FIG. 3a is a perspective view of the anti-reflux valve, illustrating the distal end of the check valve in a collapsed position within the catheter.

A check valve 30 is adapted to be received within the catheter 12, with the check valve 30 including a proximal end 32 having a perimeter 34 bonded to an inside periphery of an interior surface 16 of the catheter 12. The proximal end 32 is oriented toward the first end 14 of the catheter 12, and therefore is oriented toward the patient. The proximal end 32 remains in a substantially open configuration 36 for passage of fluids therethrough (see FIGS. 1 and 2a). The check valve 30 includes a length of flexible material that forms continuous side walls 38 that are pliable in a length dimension (see FIGS. 2a and 3a). The side walls 38 of flexible material form continuous surfaces that channel discharge fluids to a distal end 40 of the check valve 30. The flexible material of the side walls 38 can include material that is known to those skilled in the art to allow sterilization while maintaining pliability of the flexible material. The distal end 40 is oriented toward the catheter second end 18 that is releasably connected to a collection reservoir 82. The distal end 40 of the check valve 30 may remain in a partially open 42 configuration as discharge fluids 80 drain in a preferred direction 22 through the proximal end 32 and the distal end 40, and toward the catheter second end 18 and into the collection reservoir 82.

Figure 3B:
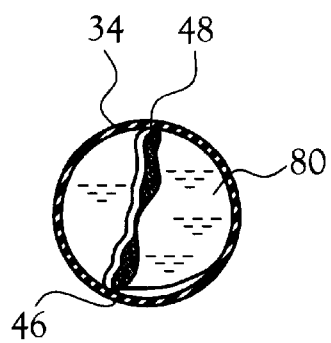
FIG. 3b is an end view of FIG. 3a, illustrating the distal end of the check valve in a collapsed position.
Figure 3C:
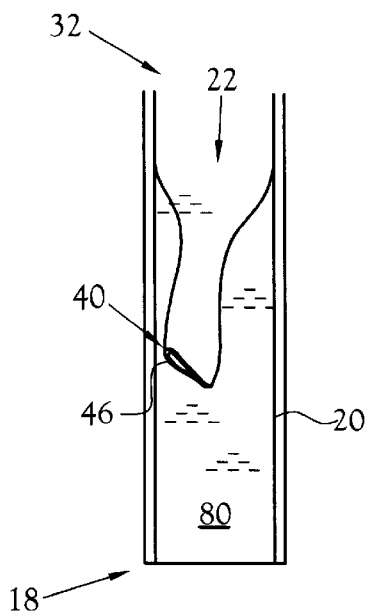
FIG. 3c is a side view of FIG. 3b, illustrating the stoppage of reflux flow of discharge liquids by the collapsed distal end of the check valve.

The distal end 40 is preferably biased to a closed configuration 48 (see FIG. 3b) after discharge of fluids therethrough, with the distal end 40 remaining collapsible upon itself when any significant amount of refluxed fluid applies back pressure against the distal end 40 (see FIG. 3c). The distal end 40 includes a flexible perimeter edge 46 formed by the distal ends of the length of flexible material 38. The orientation of the check valve 30 within the catheter 12 allows flow of fluids from the catheter first end 14, through the valve proximal end 32, through the valve distal end 40, and to the catheter second end 18. The valve distal end 40 stops reflux of fluids after discharge from the valve distal end 40 due to the closure of the flexible perimeter edge 46 of the distal end 40 to a collapsed position 48.

Figure 4:
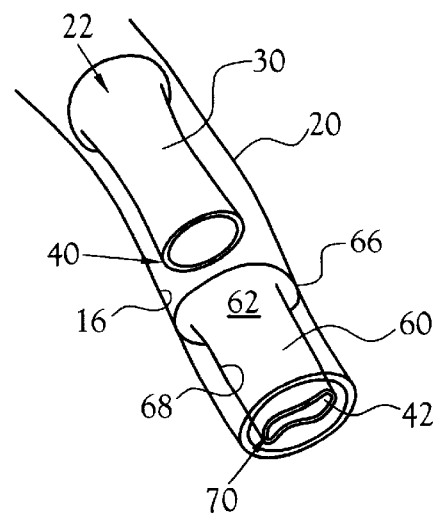
FIG. 4 is a perspective view of two check valves aligned in series with an open first valve having flow therethrough, and a second valve collapsed due to the pressure of reflux fluid from a collection reservoir.
Figure 5:
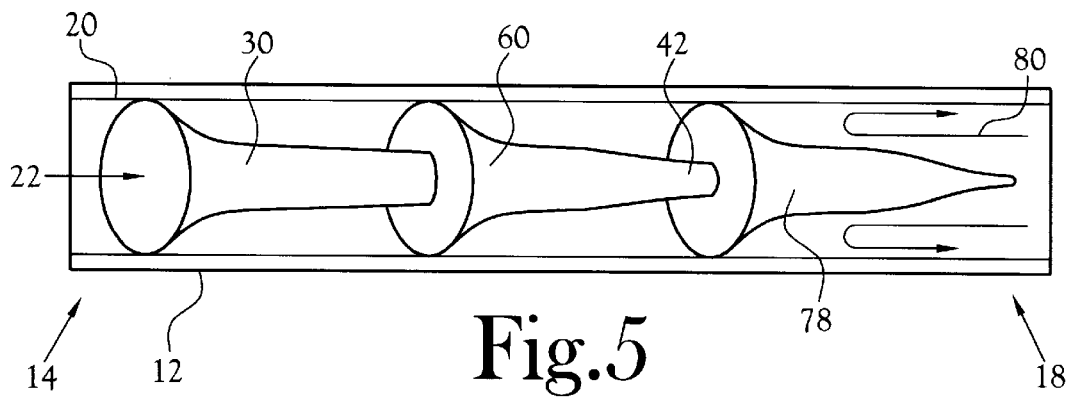
FIG. 5 is a perspective view of an anti-reflux valve system of the present invention including a plurality of check valves aligned in series within a segment of a catheter.

One embodiment of the anti-reflux valve 10 includes at least one check valve 30 positioned within an interior section of a catheter 12 (see FIGS. 1, 2a, 2b, 3a, and 3b). An alternative embodiment of the anti-reflux valve 10 includes two check valves 30, 60 aligned in series within an interior section of a catheter 12 (see FIG. 4). The distal end 40 of the first check valve 30 is aligned with a proximal end 62 of a second check valve 60, with a distal end 70 of the second check valve 60 oriented toward the catheter second end 18 and the collection reservoir 82. The second check valve proximal end 62 includes a perimeter 66 bonded to an inside periphery of the interior surface 16 of the catheter 12. The proximal end 62 remains substantially open for passage of fluids therethrough that pass through first check valve distal end 40. A distal end 70 of the second check valve 60 is biased to a closed configuration after discharge therethrough of fluids, with the second valve distal end 70 oriented toward the catheter second end 18. A length of flexible material 68 forms continuous walls of the second check valve 60, with the length of flexible material 68 being pliable in a length dimension. An additional alternative embodiment of the anti-reflux valve 10 includes a series of a plurality of check valves aligned within a catheter 12 (see FIG. 5). The plurality of check valves includes a first check valve 30 shown in an open position 36, a second check valve 60 shown in a partially closed position 42, and a third check valve 78 shown in a collapsed position 48. A plurality of check valves provides increased success in stoppage of reflux of discharge liquids 80, thereby reducing the risk of infection from exposure of discharge fluids 80 to the patient during long-term use of a plurality of anti-reflux valves 10 of the present invention.

A method of utilization of the anti-reflux valve is also disclosed for use of one or more check valves 30, 60 within a catheter 12 providing drainage of fluids from a patient as part of a medical procedure practiced in a sterile environment. The method includes providing a sterilized segment of a catheter 12 having at least one check valve 30 therein. The sterilized catheter segment is removably connected between a catheter implanted in a patient, and a tube leading to a collection reservoir 82. The method of utilization includes inspecting the sterilized catheter segment having at least one check valve therein for continuous one-way flow of fluids from the patient. Periodically, a detaching step occurs with the sterilized catheter segment detached from the catheter implanted in a patient, with replacement with a like configured sterilized catheter segment having at least one check valve 30 therein. Therefore, a detachable catheter segment is provided having at least one check valve 30 that is easily disconnectable and replaced with a like configured catheter segment having one check valve 30 therein, or replaced with a like configured catheter segment having at least two check valves 30, 60 therein, while maintaining sterile conditions within portion of the catheter upgradient of the anti-reflux valve 10 of the present invention.

From the foregoing description, it will be recognized by those skilled in the art that an anti-reflux valve is disclosed including a check valve adapted to be received within a catheter. The anti-reflux valve may include an alternative embodiment having two check valves interdisposed in series in an aligned orientation within a catheter. The anti-reflux valve may further include an alternative embodiment having a plurality of check valves interdisposed in series in an aligned orientation within a catheter to minimize the potential of reverse flow of fluids after being discharged from the most distal end of the series of check valves. Further, a means for disconnection may be included at opposed end of a segment of catheter having one or more check valves interdisposed therein to allow rapid replacement of a sterile segment of a catheter having check valves interdisposed therein when catheter tubing is replaced for a patient, thereby minimizing the possibility of infection of the patient due to the reflux of non-sterile bodily fluids.

While the present invention has been illustrated by description of several embodiments and while the illustrative embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicants' general inventive concept.

What is claimed is:

1. An anti-reflux valve sized to be disposed within a catheter for one-way passage of fluids from a patient and to a collection reservoir, comprising:

a catheter having a first end adapted to be inserted into the patient, and having a second end adapted to be releasably attached to the collection reservoir, and having a body segment having a substantially continuous interior surface extended between said first and second ends;

a check valve adapted to be received within said catheter, including:

a proximal end having a perimeter bonded along a periphery to said interior surface of said catheter, said proximal end oriented toward said first end of said catheter, said proximal end remains substantially open for passage of fluids therethrough;

a distal end being biased to closure after discharge of fluids through said distal end, said distal end oriented toward said second end of said catheter; and a length of flexible material forming continuous walls of said check valve, said length of flexible material being extended between said proximal end and said distal end, said length of flexible material being pliable along a length dimension;

wherein said check valve allows flow of fluids from said catheter first end through said proximal end and through said distal end toward said catheter second end, but restricts reverse flow of fluids after being discharged from said distal end of said check valve.

2. The anti-reflux valve of claim 1 wherein said perimeter of said proximal end is bonded along said periphery to said interior surface of said catheter, said perimeter of said proximal end being generally rigid to maintain a proximal opening for passage of fluids therethrough.

3. The anti-reflux valve of claim 1 wherein said catheter includes a catheter segment having a first end connectable to said second end of said catheter and having a second distal end connectable to the collection reservoir, said catheter segment having a second check valve adapted to be disposed therein, said second check valve is substantially like configured as said check valve interdisposed in said catheter, said second check valve having a flexible distal end being unsupported within said catheter segment with said flexible distal end of said second check valve disposed proximal of said second distal end of said catheter segment for one-way passage of fluids through said catheter segment and into the collection reservoir.

4. The anti-reflux valve of claim 3 wherein said catheter segment having said check valve interdisposed within is a sterilized unit that is interchangeable with a substantially like configured catheter segment having a substantially like configured check valve interdisposed within.

5. A discharge valve interdisposed within a catheter for one-way passage of fluids from a patient, comprising:

a check valve interdisposed within an interior of a tubular segment of the catheter, said tubular segment having a substantially continuous interior surface, said check valve including:

a proximal end having a perimeter bonded to said substantially continuous interior surface of said tubular segment, said proximal end perimeter provides an opening for passage of fluids therethrough, and a distal end biased to be collapsed upon itself after discharge of fluids therethrough; and said tubular segment having a discharge end adapted to be detachably connected to tubing in fluid communication with a discharge reservoir;

wherein said check valve allows flow of fluids through said proximal end opening but restricts the reverse flow of reflux fluids into said distal end after discharge from said distal end of said check valve.

6. The discharge valve of claim 5 wherein said perimeter of said proximal end is bonded to a periphery of said substantially continuous interior surface of said tubular segment of the catheter, said perimeter of said proximal end being generally rigid to maintain a proximal opening of the check valve within said tubular segment for passage of fluids therethrough.

7. The discharge valve of claim 6 wherein said tubular segment includes an upstream end opposed from said discharge end, said upstream end being adapted to be disconnectable from the catheter.

8. The discharge valve of claim 6 wherein said tubular segment having said check valve interdisposed within is disconnectable from said tubing and is interchangeable with a like configured second tubular segment having a substantially continuous interior surface in which a second check valve is interdisposed within.

9. An anti-reflux valve interdisposed within a catheter for one-way passage of fluids from a patient and to a collection reservoir, comprising:

a catheter having a first end adapted to be removably inserted into a patient, having a tubular body having a substantially continuous interior surface, and having a second end adapted to be releasably attached to a collection reservoir;

a first and a second check valve adapted to be aligned in series within said tubular body of said catheter, including:

a proximal end of said first check valve having a perimeter connected along a periphery of an interior surface of said catheter, said proximal end of said first check valve oriented toward said first end of said catheter, said proximal end remains substantially open for passage of fluids therethrough;

a distal end of said first check valve being biased to closure after discharge of fluids through said first check valve distal end, said distal end oriented toward said second end of said catheter; and a length of flexible material forming continuous walls of said first check valve, said length of flexible material being extended between said proximal end and said first check valve distal end, said length of flexible material being pliable in a length dimension;

a proximal end of said second check valve having a perimeter connected along a periphery of an interior surface of said catheter, said proximal end of said first check valve oriented toward said first check valve distal end, said proximal end remains substantially open for passage of fluids therethrough;

a distal end of said second check valve being biased to closure after discharge of fluids through said second check valve distal end, said second check valve distal end oriented toward said second end of said catheter; and a length of flexible material forming continuous walls of said second check valve, said length of flexible material being extended between said second check valve proximal end and said second check valve distal end, said length of flexible material being pliable in a length dimension;

wherein said first and said second check valves allow flow of fluids from said catheter first end through said respective first and said second check valves toward said catheter second end, but reverse flow is substantially restricted for fluids being discharged from said second check valve distal end.

10. The anti-reflux valve of claim 9 wherein said perimeter of each proximal end of said first and second check valve is bonded to said periphery of said substantially continuous interior surface of said catheter, said perimeter of each proximal end being generally rigid to maintain a proximal opening for passage of fluids therethrough.

11. The anti-reflux valve of claim 9 wherein said first and second check valves are interdisposed within a catheter segment having opposed ends being adapted to be disconnectable from said catheter between said first end and said second end of said catheter.

12. The anti-reflux valve of claim 11 wherein said catheter segment having said first and second check valves interdisposed within is a sterilized unit that is disconnectable from said catheter and is interchangeable with a like configured sterilized unit including a catheter segment having a first and second check valve interdisposed within.

13. An anti-reflux valve interdisposed within a catheter for one-way passage of fluids from a patient, comprising:

a catheter including a tube segment having a first end sized to be removably insertable in the patient, said tube segment having a substantially continuous interior surface, and having a discharge end connectable to a reservoir in which removed fluids are collected; and a check valve having a body composed of flexible material and adapted to be disposed within said catheter tube segment, said check valve including:

a proximal end having a perimeter bonded to said interior surface of said tube segment; and a distal end being biased to closure after discharge of fluids therethrough, said distal end being unsupported within said catheter tube segment and being oriented to release fluid proximal of said catheter discharge end;

wherein said check valve allows passage of fluids through said distal end and toward said catheter discharge end for one-way passage of fluids from said catheter discharge end.

14. The anti-reflux valve of claim 13 wherein said perimeter of said check valve proximal end is maintained in a substantially open orientation against said interior surface of said tube segment for passage of fluids therethrough.

15. The improved catheter anti-reflux valve of claim 13 wherein said distal end is substantially cylindrical in cross-section when in an open configuration for passage of fluid therethrough from said proximal end, said distal end is substantially flattened when collapsed upon itself by reversed fluid flow against said distal end from said catheter discharge end, thereby blocking reversed fluid flow from passage past said collapsed distal end and toward said check valve proximal end.

16. An anti-reflux valve system packaged as a sterilized unit, comprising:

a tube segment having a first end sized to be connectable for receipt of fluids from a catheter, said tube segment having a substantially continuous interior surface, and having a discharge end sized to be releasably connectable to a reservoir in which fluids are collected; and a check valve having a body composed of flexible material and adapted to be interdisposed within said tube segment, said check valve including:

a proximal end having a perimeter bonded to said interior surface of said tube segment; and a distal end being biased to closure after discharge of fluids therethrough, said distal end being unsupported within said tube segment and being oriented to release fluid proximal of said discharge end; a sterilized package having said tube segment disposed therein;

wherein said tube segment having said check valve interdisposed within is removable from said sterilized package for replacement of a substantially similar configured tube segment having a substantially similar check valve interdisposed within.

* * * * *